United States Patent
Mathys et al.

(10) Patent No.: US 7,112,711 B2
(45) Date of Patent: Sep. 26, 2006

(54) ALKENE OLIGOMERIZATION PROCESS

(75) Inventors: Georges Marie Karel Mathys, Korbeek-Lo (BE); Jihad Mohammed Dakka, Whitehouse Station, NJ (US); Machteld Maria Mertens, Boortmeerbeek (BE); Johan A. Martens, Huldenberg (BE); Igor V. Mishin, Moscow (RU); Raman Ravishankar, Singapore (SG); Roger Eijkhoudt, Breda (NL)

(73) Assignee: ExxonMobil Chemical Patents Inc., Houston, TX (US)

( * ) Notice: Subject to any disclaimer, the term of this patent is extended or adjusted under 35 U.S.C. 154(b) by 345 days.

(21) Appl. No.: 10/257,488

(22) PCT Filed: Apr. 20, 2001

(86) PCT No.: PCT/US01/12891

§ 371 (c)(1),
(2), (4) Date: Apr. 14, 2003

(87) PCT Pub. No.: WO01/83407

PCT Pub. Date: Nov. 8, 2001

(65) Prior Publication Data

US 2004/0006250 A1    Jan. 8, 2004

(30) Foreign Application Priority Data

Apr. 28, 2000 (GB) .................. 00104331

(51) Int. Cl.
C07C 2/02 (2006.01)
C07C 2/04 (2006.01)

(52) U.S. Cl. ............... 585/533; 585/510; 585/520; 585/530; 585/532

(58) Field of Classification Search ........... 585/510, 585/520, 530, 533, 532
See application file for complete search history.

(56) References Cited

U.S. PATENT DOCUMENTS

| | | | | |
|---|---|---|---|---|
| 4,517,399 A | | 5/1985 | Chester et al. ............. | 585/533 |
| 4,767,554 A | * | 8/1988 | Malito et al. .............. | 508/162 |
| 4,873,067 A | | 10/1989 | Valyocsik et al. .......... | 423/279 |
| 4,973,781 A | | 11/1990 | Valyocsik et al. .......... | 585/467 |
| 5,552,357 A | | 9/1996 | Lago et al. ................ | 502/63 |
| 5,571,768 A | | 11/1996 | Chang et al. .............. | 502/64 |
| 5,610,112 A | | 3/1997 | Lago et al. ................ | 502/63 |
| 5,612,270 A | | 3/1997 | Beck et al. ............... | 502/64 |
| 5,625,104 A | | 4/1997 | Beck et al. ............... | 585/475 |
| 5,993,642 A | | 11/1999 | Mohr et al. ............... | 208/46 |
| 6,039,864 A | | 3/2000 | Mohr et al. ............... | 208/134 |

FOREIGN PATENT DOCUMENTS

| | | |
|---|---|---|
| EP | 0 174 121 B1 | 3/1986 |
| EP | 0 196 602 | 3/1986 |
| EP | 0 224 220 A1 | 6/1987 |
| EP | 0 568 566 B1 | 11/1993 |
| EP | 0 793 634 B1 | 9/1997 |
| EP | 0 808 298 B1 | 11/1997 |
| JP | 7096137 | 4/1995 |
| WO | WO 93/16020 | 8/1993 |
| WO | WO 95/22516 | 8/1995 |

\* cited by examiner

*Primary Examiner*—Glenn Caldarola
*Assistant Examiner*—In Suk Bullock
(74) *Attorney, Agent, or Firm*—Andrew B. Griffis

(57) ABSTRACT

A process for oligomerising alkenes having from 3 to 6 carbon atoms which comprises contacting a feedstock comprising a) one or several alkenes having x carbon atoms, and, b) optionally, one or several alkenes having y carbon atoms, x and y being different, with a catalyst containing a zeolite of the MFS structure type, under conditions to obtain selectively oligomeric product containing predominant amounts of certain oligomers. The process is carried out at a temperature comprised between 125 and 175° C. when the feedstock contains only alkenes with 3 carbon atoms and between 140 and 240° C., preferably between 140 and 200° C. when the feedstock contains comprises at least one alkene with 4 or more carbon atoms.

19 Claims, 3 Drawing Sheets

ALKENE OLIGOMERIZATION PROCESS

Figure 1:
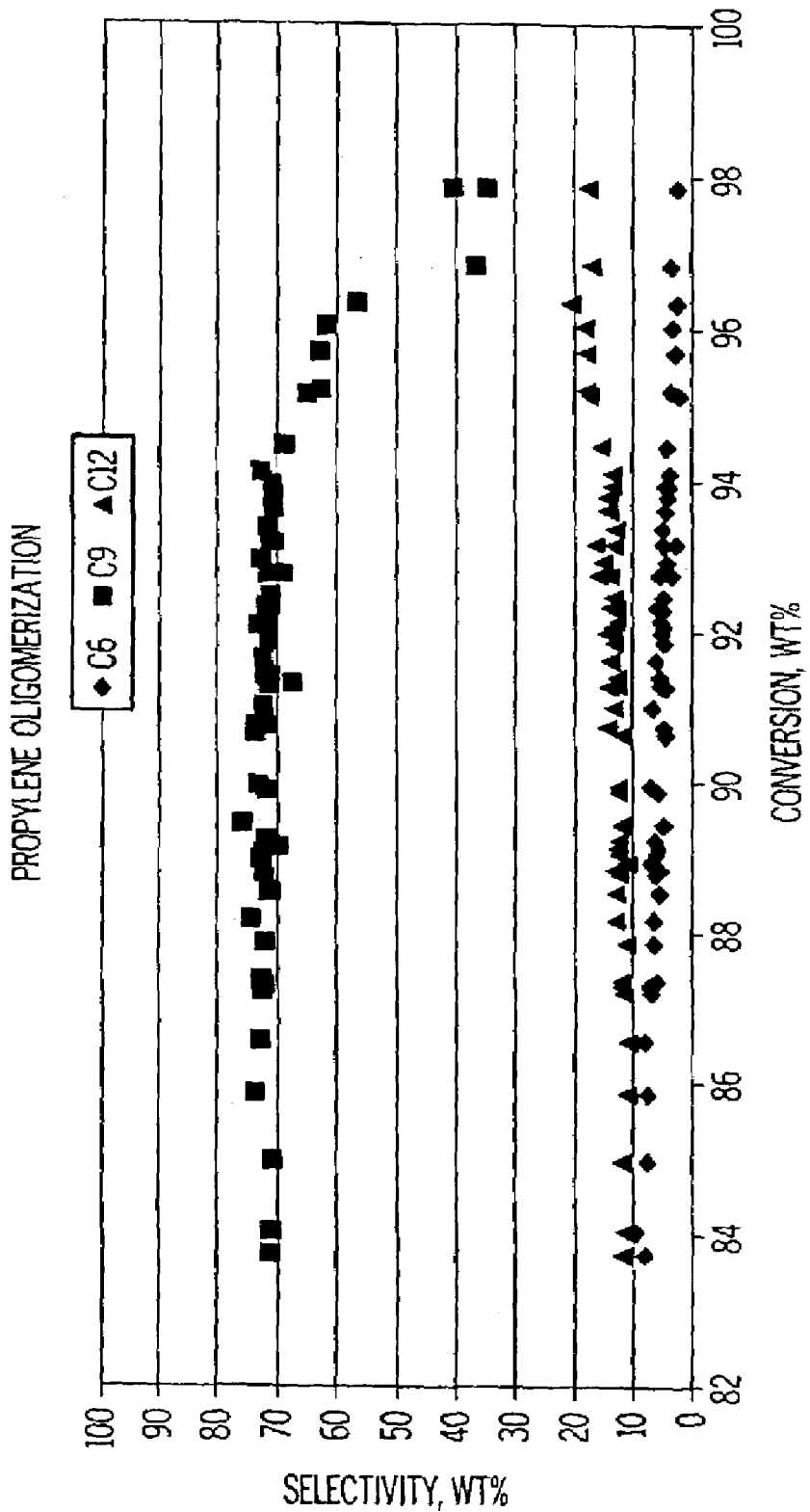

The invention relates to processes for the selective oligomerization of alkenes having from 3 to 6 carbon atoms into certain oligomers. It also relates to products obtained by these processes.

Higher alkenes are intermediate products in the manufacture of hydrocarbon solvents, higher alcohols, aldehydes and acids. They are typically produced by oligomerization of feedstreams containing alkenes with 2 to 12 carbon atoms by contacting the feedstream with an oligomerization catalyst. Solid phosphoric acid (SPA) has been widely used for this purpose. However, SPA produces significant amounts of undesired cracked products, it cannot be regenerated and has to be disposed of when its activity is no longer satisfactory.

Various zeolites have been proposed as an alternative to SPA as oligomerization catalysts. For example, U.S. Pat. No. 4,517,399 reports an olefin oligomerization process in which a feedstock containing olefins is passed over a ZSM-5 zeolite catalyst. Conditions typically reported are temperatures of 177° C. to 343° C., pressures of 100 to 5000 psig (about 0.7 MPa to 34.5 MPa) and weight hourly space velocities (WHSV) of 0.1 to 10 weight/weight.hour. U.S. Pat. No. 5,571,768, U.S. Pat. No. 5,612,270, U.S. Pat. No. 5,552,357, U.S. Pat. No. 5,625,104 and U.S. Pat. No. 5,610,112 indicate the use of selectivated forms of ZSM-5 and of other zeolites having a constraint index from 1 to 12, namely, ZSM-11, ZSM-12, ZSM-22, ZSM-23, ZSM-35, ZSM-48, ZSM-50 and ZSM-57 in olefin oligomerization under the same conditions.

WO 93/16020 discloses an alkene oligomerization process using an alkene feedstock having a water content of from 0.05 to 0.25 molar %, based on the hydrocarbon content of the feedstock. This water-containing feedstock is contacted with a zeolite catalyst selected from zeolites of the TON (H-ZSM-22, H-ISI-1, H-Theta-1, H-Nu-10, KZ-2), MTT (H-ZSM-23, KZ-1), MFI (H-ZSM-5), MEL (H-ZSM-11), MTW (H-ZSM-12) or EUO (EU-1) structure types, H-ZSM-57, zeolites of the ferrierite structure family, offretites, H-ZSM-4, H-ZSM-18, Zeolite-Beta, faujasites, zeolite L, mordenites, errionites and chabazites. Hydration of the feedstock improves the yield of oligomerization and extends catalyst life, compared with a process using a non-hydrated alkene feedstock. Suitable operating temperatures are from 180 to 255° C.

The examples of WO 93/16020 describe oligomerization of propene over H-ZSM-5, H-ZSM-12 and H-ZSM-22 and of n-butene over H-ZSM-22. For propene, typical temperatures of 170 to 250° C., pressures of 7 MPa and WHSV of 1.19 to 2.40 weight/weight.hour are used. For n-butene, reaction temperatures of 205 to 255° C., pressures of 7 MPa and WHSV of 1.75 to 2.40 weight/weight.hour are used.

These prior published proposals for olefin oligomerization all have their advantages and disadvantages, the latter including an insufficient ability to control the extent of oligomerization. For example, in the oligomerization of propene, the oligomer product contains dimers, trimers, tetramers and pentamers. There is however an increased commercial need for higher alkene products containing a predominant amount of alkenes having from 8 to 12 carbon atoms, especially nonenes. It would thus be very advantageous to have alkene oligomerization processes that are highly selective for specific oligomers.

WO 95/22516 discloses an olefin oligomerization process with improved selectivity to certain oligomers. The process is carried out over a catalyst comprising at least one molecular sieve having a refined constraint index greater than 10 and at least one molecular sieve having a refined constraint index within the range of from 2 to 10. Examples of molecular sieves having a refined constraint index greater than 10 include ZSM-22, ZSM-23 and certain ferrierites. Examples of molecular sieves having a constraint index within the range of from 2 to 10 include ZSM-5, 11, 12, 35, 38, 48 and 57, SAPO-11, MCM-22 and erionite. Oligomerization conditions are: temperature of from 170° C. to 300° C., preferably from 170° C. to 260° C., most preferably from 180° C. to 260° C., at a pressure in the range of from 5 to 10 MPa, preferably 6 to 8 MPa, with an olefin WHSV in the range of 0.1 to 20, preferably from 1 to 10, most preferably from 1.5 to 7.5 weight/weigh.hour. The feed may be hydrated before contacting the zeolite. The examples of WO 95/22516 disclose propene oligomerization over mixtures of ZSM-22 and ZSM-5 and ZSM-22 and ZSM-57 at temperatures ranging from 195 to 245° C. and conversions of 85–95%. Product selectivities obtained with the molecular sieve mixtures are compared with those obtained under the same conditions with each individual molecular sieve. The results show that molecular sieve mixtures give higher selectivities for nonenes than each molecular sieve taken alone. The best reported nonene selectivity is achieved with a 50:50 mixture of ZSM-22 and ZSM-5.

We have now unexpectedly found other alkene oligomerization conditions which give an oligomeric product containing a high proportion of a certain oligomer species. Furthermore, selectivity to certain oligomer types is also achieved when the feedstock contains alkenes with different numbers of carbon atoms.

Accordingly, the invention relates to a process for oligomerising alkenes having from 3 to 6 carbon atoms which comprises contacting a feedstock comprising
  a) one or several alkenes having x carbon atoms, and
  b) optionally, one or several alkenes having y carbon atoms, x and y being different,
with a catalyst containing a zeolite of the MFS structure type, under conditions to obtain selectively an oligomeric product, in which
  i) when the feedstock contains only alkenes having x carbon atoms, said oligomeric product contains at least 60 wt % of oligomers having 2x or 3x carbon atoms, or
  ii) when the feedstock contains alkenes having x carbon atoms and alkenes having y carbon atoms, said oligomeric product contains a mixture of oligomers containing predominant amounts of oligomers having x+y carbon atoms and of oligomers having 2x or 3x carbon atoms,
the percentages by weight being expressed with respect to the total weight of alkenes in the feedstock,
wherein the process is carried out at a temperature of from 125 to 175° C. when the feedstock contains only alkenes with 3 carbon atoms and from 140 to 240° C., preferably between 140 and 200° C., when the feedstock comprises at least one alkene with 4 or more carbon atoms.

The invention is based on the selection of a specific zeolite structure type and of a specific reaction temperature range, lower than the temperatures typically used for this type of reaction. Under these specific conditions high selectivities for certain oligomers can be achieved. The selected zeolite has the MFS structure type, as defined by the IZA structure commission and published in "Atlas of Zeolite Structure Types" by W. M. Meier et al., 4th revised Ed. Elsevier, London 1996.

The invention may be described in two specific embodiments. In the first embodiment, the alkene-containing feedstock contains one or several alkenes having x carbon atoms.

In this case, dimers or trimers form with high conversion and high selectivity. The dimers or trimers may account for at least 60 wt % of the product, based on the alkenes in the feed. For example, propene is selectively converted to nonenes, butenes are selectively converted to octenes. This may be achieved at temperatures which are lower than the temperatures previously reported for these alkenes. Despite the lower temperature, very high conversion rates may be achieved, together with very high selectivities. One would not expect simultaneous increase in selectivity and conversion at lower temperatures than those previously reported and typically practised.

In the second embodiment, the feedstock contains at least one alkene having x carbon atoms and at least one alkene having y carbon atoms, y being different from x. In this case, the process yields predominantly a dimer or trimer of the alkene having x carbon atoms and a co-oligomer having x+y carbon atoms. For example, a feedstock containing a mixture of butenes and pentenes may produce predominant amounts of nonenes (co-oligomer having x+y carbon atoms) and octenes (butene dimer). A predominant amount is defined in the present context as meaning that either the co-oligomers of x+y carbon atoms or the homo-oligomers represent at least 25 wt % of the oligomeric product and that the other major oligomer type represents at least 20 wt % of the oligomeric product, so that the sum of both predominant oligomers represents at least 45 wt %, preferably 50 wt %, and most preferably 55 wt % of the oligomeric product, based on the total weight of alkenes in the feedstock. As in the first embodiment, such selectivity may be achieved at relatively low temperatures and at high alkene conversion. Furthermore, selectivity is not affected by the alkene isomer ditribution in the feed.

In this embodiment, the molar ratio of alkenes with x carbon atoms relative to the alkenes with y carbon atoms is preferably from 10:90 to 90:10, more preferably from 25:75 to 75:25, most preferably from 45:55 to 55:45.

The alkenes in the feedstock are selected from propene (also referred to as propylene) and linear and/or branched alkenes having from 4 to 6 carbon atoms. The feedstock may contain a single alkene type, mixtures of linear and branched alkenes with the same carbon number or mixtures of linear and/or branched alkenes with different carbon numbers. For example, suitable $C_3$ and $C_4$ olefinic feeds include $C_4$ hydrocarbon mixtures obtained in refining, cracking (catalytic cracking or steam cracking) and/or reforming of oils, butane-butene fractions obtained by removing butadiene from $C_4$ by-product fractions formed in the production of ethylene by thermal cracking of oils (such fractions contain mixtures of n-butenes and isobutylene having from a few wt % of isobutylene up to 30 to 40 wt % isobutene) or $C_4$ hydrocarbon mixtures obtained by dehydrogenation of hydrocarbon mixtures containing n-butane and isobutane.

For feedstocks containing $C_4$ alkenes, a particular embodiment of the invention relates to processes using a feedstock in which isobutylene represents from 12 to 34 wt %, preferably from 12 to 20 wt % of the total weight of the feedstock. For such feedstocks, the process gives an oligomeric product that contains from 8 to 25 wt % trimethylpentenes, preferably from 8 to 16 wt % trimethylpentenes with respect to the total weight of octenes in the oligomeric product.

Such processes enable to obtain octene compositions in which the amount of octene oligomers with tetra-substituted double bonds represents between 10 and 15 mole % of the total amount of octene oligomers. Also, the average branchiness of the octenes ranges from 1.60 to 1.85. These octene composition characteristics are associated with improved reactivity when the octene compositions are submitted to hydroformylation.

The feedstock may also comprise from 0.05 to 0.25 molar % water, more preferably from 0.06 to 0.20 molar % water, most preferably from 0.10 to 0.20 molar % water based on the total hydrocarbon content of the feedstock. If necessary, the water content of the feedstock may be increased by any suitable means. For example, the feedstock can be passed through a thermostatted water saturator. Since the amount of water required to saturate the alkene feedstock will depend upon the temperature and composition of the feedstock, control of the water content can then be effected by appropriate control of the temperature of the feedstock.

The feedstock may also comprise an inert diluent. If the diluent is a hydrocarbon gas other than an alkene having from 3 to 6 carbon atoms, such as, for example, a saturated hydrocarbon gas, that other hydrocarbon is to be included in the hydrocarbon content for the purposes of calculation of the water content. The feedstock may also comprise ethylene and/or alkenes having 7 or more carbon atoms. In this case, the other alkenes are also to be included in the hydrocarbon content for the purposes of calculation of the water content.

The catalyst contains a zeolite of the MFS structure type, such as ZSM-57 as disclosed in EP-B-174121, U.S. Pat. No. 4,873,067 and U.S. Pat. No. 4,973,781 herewith incorporated by way of reference. Zeolite catalysts having crystal structures that are essentially the same as the MFS crystal structure but differ slightly therefrom in chemical composition may also be used, such as, zeolite catalysts obtained by removal of a number of aluminium atoms from, or by steaming of the zeolite, or zeolite catalyst obtained by addition of different elements, for example, by impregnation or cation exchange or by incorporation during the zeolite synthesis.

ZSM-57 crystals may be prepared by any suitable method, for example, by heating a reaction mixture containing a source of silicon oxide and a source of aluminium oxide. The crystals are then generally calcined in air or oxygen at a temperature exceeding 500° C., for example, at a temperature of 510 or 550° C. for, for example, 10 to 20 hours. The calcined material is preferably exchanged with ammonium ions ($NH_4^+$) and subjected to conditions under which the ammonium ions decompose, with the formation of ammonia and a proton, thus producing the acid form of ZSM-57. The zeolite may be fully protonated, i.e. substantially all acid sites are in proton form. Alternatively, the zeolite may be partially protonated. The acid form may also be obtained by acid exchange with, for example, hydrochloric acid.

A modified ZSM-57 may also be used. The term "modified" means ZSM-57 formed by a method in which an organic substance (organic promoter or template) is used to promote formation of aluminosilicate crystals (zeolite precursor crystals) having the desired MFS structure type. The uncalcined zeolite precursor crystals are exchanged with ammonium ions or protons, and the crystals are then calcined under conditions such that a portion of the organic promoter or of a decomposition product derived therefrom remains within the pores of the crystal.

Reference is made to the following documents disclosing the preparation of ZSM-57 or modified ZSM-57 containing catalyst: U.S. Pat. No. 4,873,067, U.S. Pat. No. 4,973,781, EP-B1-174,121, EP-A-625132 as well as Ernst and Weitkamp in "Zeolite ZSM-57: Synthesis, Characterization and Shape Selective Properties", in "Catalysis and Adsorption Zeolites", Ed. G. Öhlmann et al., Elsevier Science Publishers, B. V. Amsterdam, all incorporated by way of reference.

The zeolite crystals may in some cases contain a minor proportion of another crystalline material, such as another zeolite structure type or quartz. The zeolite of MFS structure type may be used in the form of powders (including powders consisting wholly or in part of single crystals). The zeolite crystals may instead be incorporated in shaped agglomerates, for example, tablets, extrudates or spheres, which may be obtained by combining the zeolite with a binder material that is substantially inert under the conditions employed in the oligomerization process. The zeolite catalyst may be present in amount of from 1 to 99% by weight, based on the combined weight of the zeolite and binder material. As binder material, any suitable material may be used, for example, silica, metal oxides, or clays, such as montmorillonite, bentonite and kaolin clays, the clays optionally being calcined or modified chemically prior to use. Further examples of suitable matrix materials include silica-alumina, silica-berylia, silica-magnesia, silica-thoria, silica-titania, silica-alumina-magnesia, silica-alumina-thoria, silica-alumina-zirconia and silica-magnesia-zirconia. The MFS zeolite crystals may also be bound with another zeolite as disclosed for example in U.S. Pat. No. 5,993,642, U.S. Pat. No. 6,039,864, EP-B-568,566, EP-B-793,634 and EP-B-808,298, all incorporated herewith by way of reference.

The alkene-containing feedstock is contacted with the catalyst containing a zeolite of the MFS group as defined above at a specific temperature which depends on the alkenes present in the feedstock. If the feedstock only contains propene (propylene), the reactor temperature is between 125 and 175° C., preferably between 125 and 150° C. When the feedstock contains at least one alkene having 4 to 6 carbon atoms, the reactor temperature is between 140 and 240° C., preferably between 140 and 200° C., most preferably between 140 and 175° C.

The pressure is preferably in the range of from 5 to 10 MPa, more preferably, from 6 to 8 MPa and at an alkene weight hourly space velocity preferably in the range of from 0.1 to 20, more preferably from 1 to 10, and most preferably from 1.1 to 7.5 weight/weight.hour.

A desired conversion level is generally obtained by first selecting a reaction temperature and by regularly adjusting this reaction temperature to compensate for catalyst deactivation over time. The process of the invention is highly selective at conversion rates as high as 95 wt %, typically comprised between 65 and 95 wt %, preferably comprised between 85 and 95 wt %.

The process gives a product containing an oligomeric product which can be further transformed by any one or more of the following steps: fractionation, hydrogenation, hydroformylation, oxidation, carbonylation, etherification, epoxidation, hydration. Accordingly, the present invention also concerns higher alcohols obtained by hydroformylation and hydrogenation of the oligomeric product. It also encompasses a process for the preparation of an ester of a polycarboxylic acid in which the higher alcohols derived from the oligomeric product are reacted with a polycraboxylic acid under conditions suitable to make the polycarboxylic esters. Preferred esters are phthalic or adipic esters.

Figure 2:
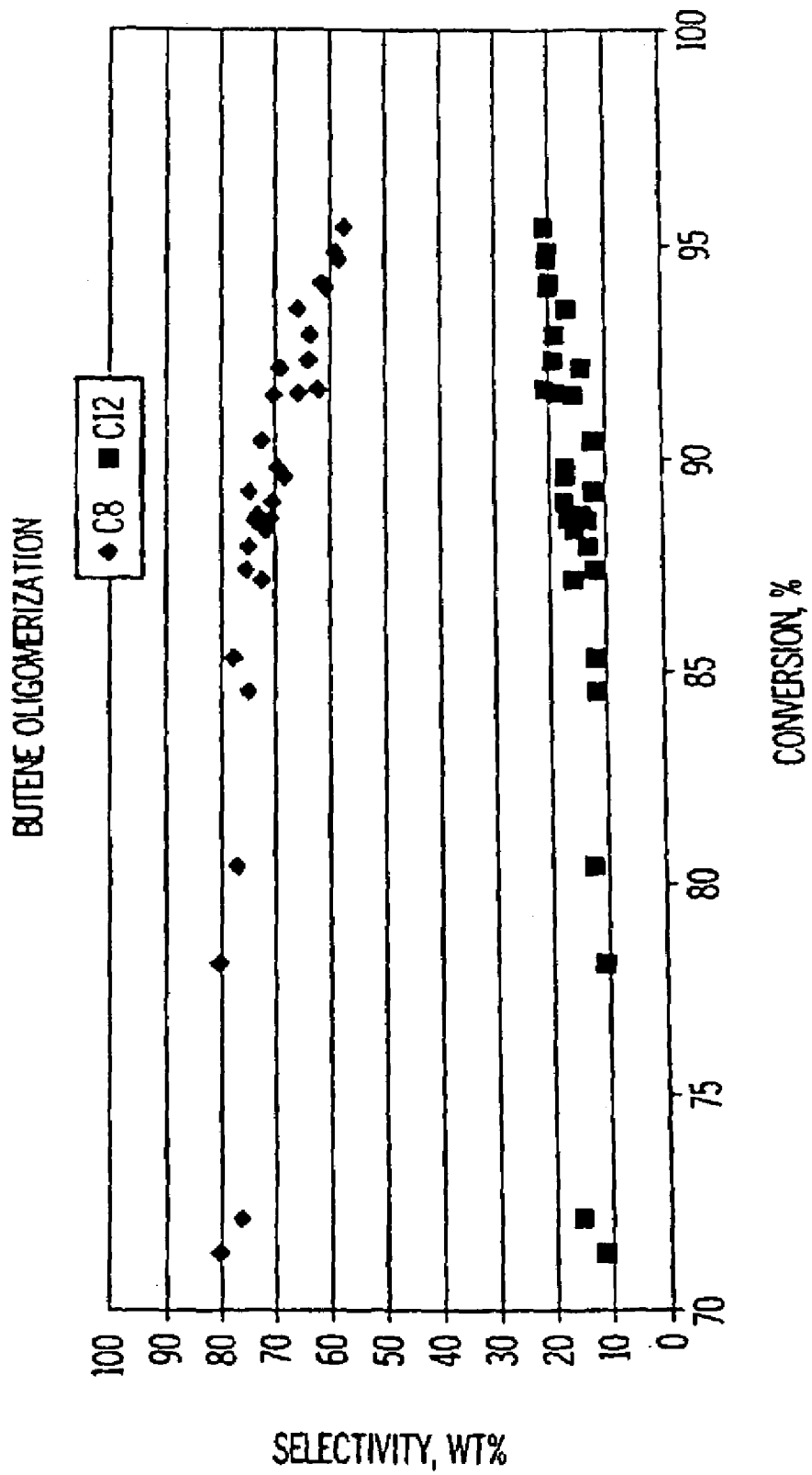
Figure 3:
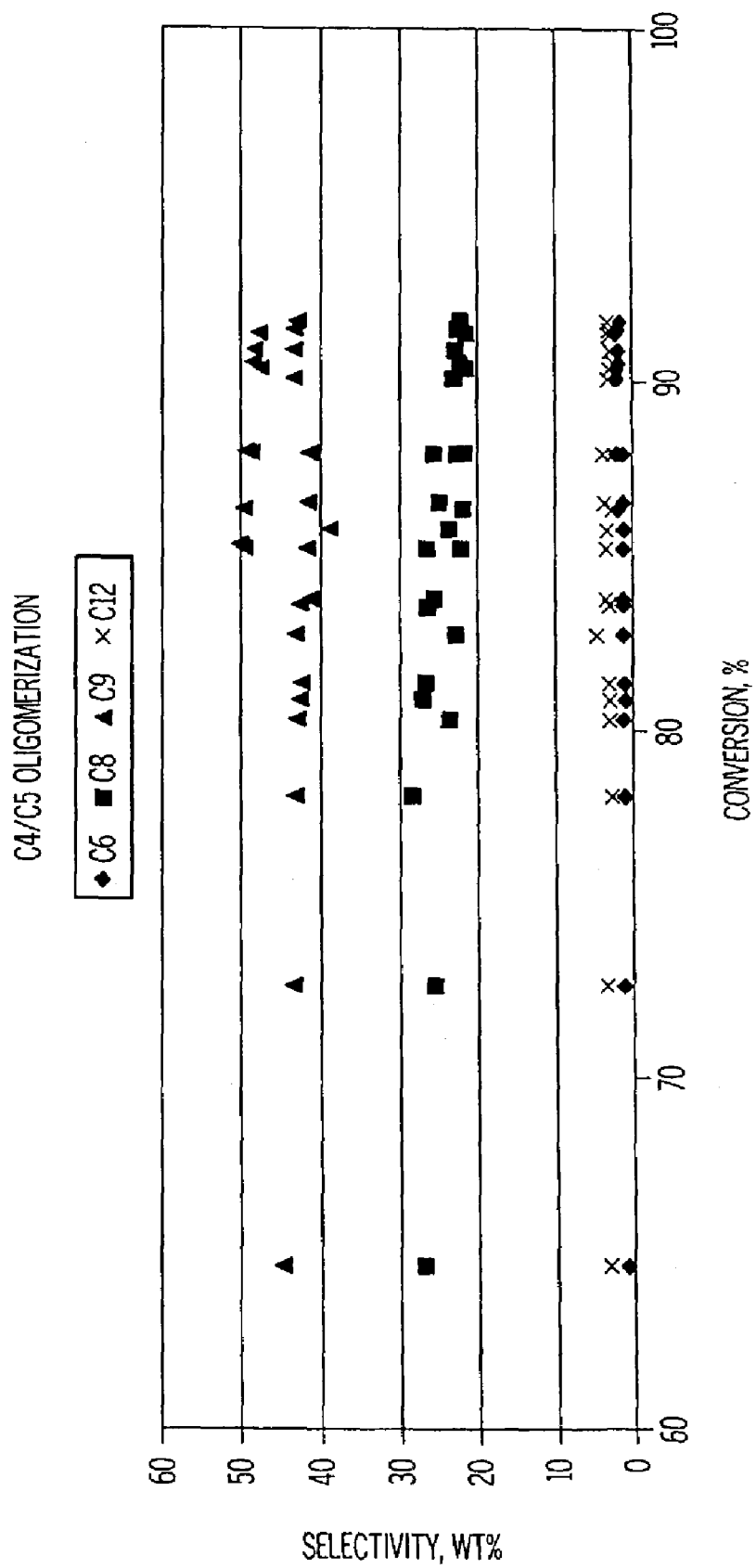

Certain illustrative embodiments of the invention will now be described with reference to the following drawings:

FIG. 1: selectivity versus conversion for propylene oligomerization;

FIG. 2: selectivity versus conversion for n-butene oligomerization;

FIG. 3: selectivity versus conversion for oligomerization of a feedstock containing butenes and pentenes.

In the following examples, conversion and selectivity are calculated according to the method disclosed in "Industrielle Organische Chemie", K. Weissermel and H.-J. Harpe, 3rd Edition, VCH, 1988.

Accordingly, the conversion was calculated based upon gas chromatographic peak areas, using as internal standard the total sum of the paraffins in the feed, using the following equation:

$$\text{Conversion } (\%) = \left[1 - \frac{A_{olefin}/A_{paraffins}}{A^0_{olefin}/A^0_{paraffins}}\right] \times 100$$

where
  A=chromatographic peak area in product analysis (wt %)
  $A^O$=chromatographic peak area in feed analysis (wt %).

The selectivity is determined from gas chromatographic peak areas, after hydrogenation of the reaction product stream according to the following equation:

$$S_{Cn} = \frac{A_{Cn}}{\sum_i A_{Ci}}$$

where
  $A_{Cn}$=chromatographic peak area of all isomers with carbon number n, and
  $A_{Ci}$=chromatographic peak area of all isomers with carbon number other than n.

EXAMPLE 1

Preparation of H-ZSM-57 Crystals

Composition A, containing 150.02 g Ludox HS40 (a colloidal silica solution from Dupont sold as 40 wt % $SiO_2$ in water) and 400.21 g demineralized water, was mixed in the beaker of a household mixer. Solution C, containing 43.3 g of N,N,N,N',N', N'-hexaethylpentanediammonium bromide (also known as Hexaethyl-Diquat-5 (bromide salt) and hereinafter abbreviated R) and 97.36 g demineralized water, was added with 11.53 g of rinse water to solution A. The resulting mixture was mixed at room temperature for 5 minutes. Composition B, containing 11.14 $Al_2(SO_4)_3.18$ $H_2O$, 16.25 g NaOH (Baker 98.6 wt %) and 99.97 g demineralized water, was than added with 12.10 g rinse water. The resulting mixture was mixed for an additional 5 minutes, giving a gel with the molar composition 2 $Na_2O$/R/0.17 $Al_2O_3$/10 $SiO_2$/400 $H_2O$.

537 g of the gel was transferred to a 1 liter stainless steal autoclave equipped with a stirrer. The autoclave was heated to 160° C. over a period of 6 hours while the mixture was stirred at 120 rpm. Heating at 160° C. and stirring were continued for 144 hours (6 days).

The content of the autoclave was transferred to a 1 liter centrifuge bottle and was washed by decanting the supernatant and re-dispersing the precipitate in demineralized water. This was repeated until the pH of the supernatant was 10.5. The washed product was dried overnight at 120° C.

This resulted in pure H-ZSM-57 crystals having a SiO$_2$/Al$_2$O$_3$ molar ratio of 41.

EXAMPLE 2

Propylene Oligomerization

H-ZSM-57 crystals synthesized as described in Example 1 were calcined in air for 16 h at 510° C., exchanged with a NH$_4$Cl aqueous solution and calcined again at 510° C. for 16 h in air. The crystals were then granulated by compressing into particles having a size of 1.1–2 mm.

A feedstock containing, on a hydrocarbon basis 50 wt % propylene, 40 wt % n-butane and 10 wt % iso-butane was hydrated by passing it at a temperature comprised between 25 and 40° C., through a thermostatted water saturator prior to its introduction into the reactor. The water content of the feedstock prior to its introduction into the water saturator was ca 0.02 molar % and on leaving the saturator was ca 0.10 to 0.15 molar % (depending on the exact hydration temperature), in each case based on the total hydrocarbon content of the feedstock. The hydrated feedstock was then passed over the-catalyst particles. The reactor effluent was analyzed at regular intervals by gas chromatography (GC) for determining the olefin conversion and product selectivity. The reactor was operated continuously for 88 days. Initially, the reactor temperature was set at 125° C.; it was progressively increased up to 172° C. to maintain alkene conversion above 80 wt %. The reactor pressure was maintained at 7 MPa.

Table 1a shows representative operating conditions and product analyses. FIG. 1 shows the selectivity for hexenes, nonenes and dodecenes as a function of propylene conversion throughout reactor operation. These results demonstrate high selectivity for the production of nonenes. Propylene conversions of 83 to 95 wt % were achieved at temperatures ranging from 135 to 170° C.

The composition of the product mixture was determined by gas chromatography (GC), using hydrogen as carrier gas. The injector liner was filled with a hydrogenation catalyst (0.03 g of 0.5% Pt on Al$_2$O$_3$) so that, by in-situ hydrogenation, all the components were identified as paraffins. Overall, the nonenes consisted of 9.47 wt % of triple-branched isomers, 84.53 wt % of double-branched isomers, 5.58 wt % of mono-branched isomers and 0.42 wt % linear isomers. Overall, the nonene products thus had an average branchiness of 2.03. Table 1b provides the detailed product composition of the C$_9$ alkene products after hydrogenation.

The conversion of propylene was determined by GC analysis without in-situ hydrogenation, by comparing the GC analysis of the product mixture with the GC analysis of the feedstock under the same conditions. The feedstock contains butane and isobutane which are inert under the reaction conditions; butane and isobutane were thus used as internal standards for calculating conversions.

TABLE 1a

Propylene oligomerization

| Sample Number | I | II | III | IV | V | VI | VII | VIII |
|---|---|---|---|---|---|---|---|---|
| Hydration Temperature (° C.) | 27 | 29 | 26 | 40 | 40 | 40 | 40 | 40 |
| Reactor Temperature (° C.) | 135 | 140 | 150 | 155 | 160 | 165 | 170 | 170 |
| WHSV (wt/wt.hr) | 1.81 | 1.94 | 2.13 | 2.7 | 3.25 | 2.22 | 2.36 | 2.89 |
| No. of days on stream | 1.2 | 8.9 | 9.9 | 41.9 | 51.9 | 56.9 | 73.9 | 83.9 |
| Total conversion (wt %) | 92.75 | 87.23 | 95.14 | 87.38 | 84.06 | 92.17 | 93.98 | 91.39 |
| C5 selectivity (wt %) | 0.11 | 0.08 | 0.1 | 0.1 | 0.17 | 0.15 | 0.12 | 0.15 |
| C6 selectivity (wt %) | 3.24 | 6.53 | 1.92 | 5.73 | 9.16 | 5.03 | 4.08 | 4.95 |
| C7 selectivity (wt %) | 1.14 | 1 | 1.57 | 1.41 | 1.83 | 1.99 | 1.96 | 1.93 |
| C8 selectivity (wt %) | 1.71 | 1.32 | 2.45 | 1.89 | 2.18 | 2.58 | 2.75 | 2.63 |
| C9 selectivity (wt %) | 71.96 | 72.78 | 65.29 | 72.64 | 70.98 | 71.5 | 72.75 | 71.3 |
| C10–C11 selectivity (wt %) | 1.5 | 0.73 | 1.91 | 1.05 | 1.24 | 1.57 | 1.62 | 1.47 |
| C12 selectivity (wt %) | 15.63 | 11.62 | 17.29 | 11.45 | 10.45 | 12.34 | 12.84 | 12.32 |
| C15 + selectivity (wt %) | 4.55 | 5.81 | 9.22 | 5.58 | 3.82 | 4.69 | 3.72 | 5.07 |
| Cracking (wt %) * | 4.63 | 3.26 | 6.28 | 4.61 | 5.59 | 6.44 | 6.62 | 6.36 |

* cracking: sum of C5, C7, C8, C10–C11 selectivities

TABLE 1b

Propylene oligomerization -Nonene oligomer identification after hydrogenation

| Nonene oligomer | Wt % |
|---|---|
| 2,2,5-trimethylhexane | 0.49 |
| 2,2,4-trimethylhexane | 0.41 |
| 2,3,5-trimethylhexane | 2.56 |
| 2,2-dimethylheptane | 2.37 |
| 2,4-dimethylheptane | 10.60 |
| 2-methyl-4-ethylhexane | 1.65 |
| 2,6-dimethylheptane | 1.22 |
| 2,5-dimethylheptane | 6.32 |
| 3,5-dimethylheptane | 3.75 |
| 2,4-dimethyl-3-ethylpentane | 3.58 |
| 2,3,3-trimethylhexane | Not detected |
| 2-methyl-3-ethylhexane | 8.54 |
| 2,3,4-trimethylhexane | Not detected |
| 3,3,4-trimethylhexane | 2.43 |
| 2,3-dimethylheptane | 19.99 |
| 3,4-dimethylheptane | 30.10 |
| 4-methyloctane | 1.44 |
| 2-methyloctane | 0.15 |
| 3-ethylheptane | 0.57 |
| 3-methyloctane | 3.42 |
| n-nonane | 0.42 |

EXAMPLE 3

Butene Oligomerization

A feedstock containing, based on hydrocarbon content, 49.5 wt % propane and 50.5 wt % butene-1, having an initial water content of ca 0.02 molar % based upon the hydrocarbon content, was hydrated a temperature of 25 to 40° C. as described in Example 2, to give a hydrated feedstock con taining 0.1 to 0.15 molar % water. This hydrated feedstock was passed over H-ZSM-57 prepared as in Example 1 and calcined at 510° C. and granulated as in Example 2. The product was analyzed by GC at regular intervals for determining olefin conversion and product selectivity. The reactor was operated continuously for 43 days. Initially, the reactor temperature was set at 125° C.; it was progressively increased up to 240° C. to maintain alkene conversion above 70 wt %. The reactor pressure was maintained at 7 MPa.

Table 2a shows representative operating conditions and product analyses. FIG. 2 shows the selectivity for octenes and dodecenes as a function of butene conversion throughout reactor operation. These results demonstrate high selectivity for the production of octenes.

The composition of the product mixture was determined by gas chromatography (GC), using hydrogen as carrier gas. The injector liner was filled with a hydrogenation catalyst (0.03 g of 0.5% Pt on $Al_2O_3$) so that, by in-situ hydrogenation, all the components were identified as paraffins. The $C_8$ alkene products contained 1.58 wt % of triple-branched isomers, 71.44 wt % of double-branched isomers, 25.46 wt % of mono-branched isomers and 1.52 wt % linear isomers. Overall, the octene products had an average branchiness of 1.73. Table 2b provides the detailed product composition of the $C_8$ alkene products after hydrogenation.

The conversion of butene-1 was determined by comparing the GC analysis of the product mixture with the GC analysis of the feedstock under the same conditions and is thus used as an internal standard.

Proton NMR analysis was used to identify the olefin type of the octene ($C_8$ oligomers) and dodecene ($C_{12}$ oligomers) fractions of the product. The olefin type is defined as follows:

| | |
|---|---|
| Type I | mono-substituted double bond: R—CH=CH2 |
| Type II | di-substituted double bond: R—CH=CH—R' |
| Type III | di-substituted double bond: RR'C=CH2 |
| Type IV | tri-substituted double bond: RR'C=CH—R'' |
| Type V | tetra-substituted double bond: RR'C=CR''R''' | where R, R', R'' and R''' each represent an alkyl group.

The octene fraction of the product contained 1.4 mole % Type I, 15.8 mole % Type II, 10.7 mole % Type III, 60.9 mole % Type IV and 11.2 mole % Type V products. The dodecene fraction of the product contained 1.0 mole % Type I, 11.8 mole % Type II, 6.6 mole % Type III, 53 mole % Type IV and 27.6 mole % Type V products.

The average branchiness of the dodecene fraction of the product was 2.8 as determined by NMR.

TABLE 2a

Butene oligomerization.

| Sample Number | I | II | III | IV | V | VI | VII | VIII |
|---|---|---|---|---|---|---|---|---|
| Hydration Temperature (° C.) | 25 | 40 | 25 | 26 | 40 | 40 | 40 | 40 |
| Reactor Temperature (° C.) | 145 | 155 | 165 | 165 | 200 | 200 | 230 | 240 |
| WHSV (wt/wt.hr) | 3 | 2.21 | 2.54 | 5.49 | 6.88 | 6.73 | 6.5 | 6.36 |
| No. of days on stream | 2 | 9 | 15 | 22 | 28 | 33 | 37 | 43 |
| Total conversion (wt %) | 89.71 | 92.04 | 94.6 | 75.09 | 94.31 | 81.71 | 94.53 | 90.37 |
| C5 selectivity (wt %) | 0.06 | 0.09 | 0.13 | 0.08 | 0.26 | 0.18 | 0.54 | 0.79 |
| C6 selectivity (wt %) | 0.21 | 0.24 | 0.29 | 0.26 | 0.36 | 0.28 | 0.56 | 0.56 |
| C7 selectivity (wt %) | 0.51 | 0.61 | 0.77 | 0.53 | 1.54 | 0.97 | 2.87 | 2.94 |
| C8 selectivity (wt %) | 65.95 | 64.3 | 61.31 | 79.08 | 63.97 | 80.11 | 64.06 | 71.38 |
| C9 selectivity (wt %) | 1.5 | 1.65 | 1.85 | 0.99 | 3.02 | 1.73 | 4.71 | 4.16 |
| C10–C11 selectivity (wt %) | 2.47 | 2.67 | 3.06 | 1.3 | 2.88 | 1.27 | 3.26 | 2.24 |
| C12 selectivity (wt %) | 19.36 | 18.41 | 18.98 | 12.75 | 16.55 | 11.3 | 14.63 | 12.18 |
| C13-C14-C15 selectivity (wt %) | 1.13 | 1.38 | 1.66 | 0.59 | 1.68 | 0.54 | 2.15 | 1.41 |
| C16 + selectivity (wt %) | 9.8 | 10.63 | 11.95 | 4.42 | 9.74 | 3.62 | 7.22 | 4.35 |
| Cracking (wt %) * | 5.89 | 6.65 | 7.76 | 3.75 | 9.74 | 4.97 | 14.09 | 12.08 |

* cracking: sum of C5, C6, C7, C9, C10–C11, C13-C14-C15 selectivities.

TABLE 2b

Butene oligomerization - Octene oligomer identification after hydrogenation.

| Octene oligomer | Wt % |
|---|---|
| 2,2,4-trimethylpentane | 0.16 |
| 2,2-dimethylhexane | 3.52 |
| 2,5-dimethylhexane | 5.08 |
| 2,4-dimethylhexane | 29.64 |
| 2,2,3-trimethylpentane | * |
| 3,3-dimethylhexane | 1.92 |
| 2,3,4-trimethylpentane | 1.23 |
| 2,3,3-trimethylpentane | 0.19 |
| 2,3-dimethylhexane | 13.77 |
| 2-methyl-3-ethylpentane | 3.59 |
| 2-methylheptane | 7.17 |
| 4-methylheptane | 4.50 |
| 3,4-dimethylhexane | 13.93 |
| 3-methylheptane | 13.79 |
| n-octane | 1.52 |
| Total | 100 |

*Overlaps with 2,4-dimethylpentane

EXAMPLE 4

Oligomerization of Feedstocks Containing Butenes and Pentenes

In this example, a feedstock containing butenes and pentenes was used. The feedstock was hydrated before entering the reactor as described in Example 2, the temperature of hydration being comprised between 33 and 40° C. The hydrated feedstock was passed over H-ZSM-57 prepared as described in Example 1 and calcined at 550° C. and granulated as described in Example 2.

The three feedstocks identified in Table 3a were used during this experiment. Throughout the experiment, the reactor pressure was maintained at 7 MPa. The reactor effluent was analyzed at regular intervals by GC. The reaction temperature was initially 202° C. and was raised progressively to 234° C. to maintain alkene conversion above 65 wt %.

Table 3b shows representative operating conditions and product analyses. FIG. 3 shows the selectivity for hexenes, octenes, nonenes and dodecenes as a function of butene and pentene conversion throughout reactor operation. These results demonstrate high selectivity for the production of octenes and nonenes, regardless of the type of pentene isomer present in the feedstock.

TABLE 3a

Feedstock compositions.

| Component (wt %) | Feedstock A | Feedstock B | Feedstock C |
|---|---|---|---|
| Iso-butane | 8.27 | 9.60 | 10.51 |
| n-butane | 5.28 | 5.79 | 5.45 |
| Butene-1 | 9.85 | 11.38 | 10.25 |
| Iso-butene | 0.80 | 0.90 | 0.88 |
| 1,3-Butadiene | 0.16 | 0.17 | 0.16 |
| Butene-2 trans | 10.37 | 10.44 | 10.13 |
| Butene-2 cis | 6.98 | 6.89 | 6.61 |
| Iso-pentane | 18.29 | 17.54 | 17.71 |
| n-Pentane | 2.32 | 2.12 | 2.22 |
| 3-Methyl-butene-1 | 0.63 | 0.66 | 0.83 |
| Pentene-2 trans | 6.20 | 5.56 | 5.73 |
| 2-Methyl-butene-2 | 0 | 24.35 | 11.25 |
| Pentene-1 | 28.81 | 0.06 | 14.21 |
| 2-Methyl-butene-1 | 0.28 | 1.83 | 1.85 |
| Pentene-2 cis | 2.27 | 2.03 | 2.17 |
| Total butenes | 28.00 | 29.61 | 27.87 |
| Total pentenes | 38.19 | 34.49 | 36.04 |
| Total iso-pentenes | 0.28 | 26.84 | 13.93 |
| Total n-pentenes | 37.28 | 7.65 | 22.11 | and 40° C. The hydrated feedstocks were passed over the catalyst. In this example, the catalyst used consisted of H-ZSM-57, prepared as described in Example 1 which had been formulated and extruded as catalyst particles. The catalyst particles were calcined at 510° C. before use.

The six feedstocks identified in Table 4 were used during this experiment. Throughout the experiment, the reactor pressure was maintained at 7 MPa. The reactor effluent was analyzed at regular intervals by GC. The reaction temperature was initially 175° C. and was adjusted to maintain a total alkene conversion above 95%.

The composition of the product mixture was determined by gas chromatography (GC), using hydrogen as carrier gas. The injector liner was filled with a hydrogenation catalyst (0.03 g of 0.5% Pt on $Al_2O_3$) so that, by in-situ hydrogenation, all the components were identified as paraffins.

The conversion of butenes/isobutene was determined by comparing the GC analysis of the product mixture with the GC analysis of the feedstock under the same conditions. The feedstock contains butane and isobutane which are inert under the reaction conditions; butane and isobutane were thus used as internal standards for calculating conversions.

Table 4 shows the conversions of n-butenes and isobutylene, the selectivity for octenes trimethylpentenes and the weight of trimethylpentene expressed as a percentage of the total weight of all oligomers formed (oligomeric product).

TABLE 3b

Oligomerization of a feedstock containing butenes and pentenes

| Sample Number | I | II | III | IV | V | VI | VII | VIII |
|---|---|---|---|---|---|---|---|---|
| Feedstock composition | A | A | A | B | B | B | C | C |
| Butenes in feed (mol %) | 48.34 | 48.34 | 48.34 | 51.68 | 51.68 | 51.68 | 49.29 | 49.29 |
| Pentenes in feed (mol %) | 51.65 | 51.65 | 51.65 | 47.86 | 47.86 | 47.86 | 50.71 | 50.71 |
| Hydration Temperature (° C.) | 40 | 40 | 40 | 40 | 40 | 40 | 40 | 40 |
| Reactor Temperature (° C.) | 215 | 217 | 217 | 222 | 227 | 232 | 234 | 234 |
| WHSV (wt/wt.hr) | 2.11 | 2.09 | 2.1 | 2.02 | 2.09 | 2.1 | 2.09 | 2.12 |
| No. of days on stream | 136.6 | 139.6 | 146.6 | 150.6 | 156.6 | 160.6 | 163.6 | 166.6 |
| Total conversion (wt %) | 85.69 | 86.45 | 78.09 | 90.55 | 87.91 | 90.41 | 91.74 | 90.13 |
| Butene conversion | 93.25 | 93.6 | 87.48 | 94.98 | 91.98 | 64.63 | 95.77 | 94.62 |
| Pentene conversion | 80.04 | 81.14 | 70.95 | 86.94 | 84.55 | 87.06 | 88.9 | 86.89 |
| C6 selectivity (wt %) | 1 | 0.93 | 0.9 | 1.81 | 1.86 | 1.83 | 1.5 | 1.79 |
| C7 selectivity (wt %) | 0.5 | 0.53 | 0.51 | 0.54 | 0.57 | 0.66 | 0.74 | 0.75 |
| C8 selectivity (wt %) | 23.79 | 25.29 | 28.51 | 22.36 | 22.78 | 21.53 | 22.32 | 23.19 |
| C9 selectivity | 39.14 | 41.8 | 43.33 | 48.76 | 48.72 | 47.93 | 43.21 | 43.69 |
| C10–C11 selectivity (wt %) | 18.61 | 19.98 | 18.39 | 17.58 | 17.0 | 17.31 | 20.27 | 20.16 |
| C12 selectivity (wt %) | 3.14 | 3.44 | 2.75 | 2.76 | 2.5 | 2.93 | 3.24 | 2.93 |
| C13 + selectivity (wt %) | 13.82 | 8.02 | 5.61 | 6.18 | 6.57 | 7.81 | 8.72 | 7.49 |

EXAMPLE 5

Oligomerization of $C_4$ Feedstocks Containing a Mixture of Linear and Branched butenes.

In this example, $C_4$ feedstocks containing a mixture of n-butenes and isobutylene were used. The feedstocks were hydrated before entering the reactor as described in Example 2, the temperature of hydration being comprised between 33

TABLE 4

Oligomerization of C4 feedstocks containing a mixture of linear and branched butenes - Feedstock composition.

|  | A | B | C | D | E | F |
|---|---|---|---|---|---|---|
| Overall $C_4$ alkene content (wt %)[1] | 66.49 | 65.8 | 65.8 | 65.8 | 66.13 | 66.13 |

TABLE 4-continued

Oligomerization of C4 feedstocks containing a mixture of linear and branched butenes - Feedstock composition.

|  | A | B | C | D | E | F |
|---|---|---|---|---|---|---|
| Isobutylene fraction (wt %)[2] | 7.93 | 13.12 | 13.12 | 13.12 | 21.95 | 21.95 |
| Isobutylene conversion (%) | 100.0 | 100.0 | 100.0 | 100.0 | 100.0 | 100.0 |
| n-Butenes conversion (%) | 94.52 | 94.74 | 92.83 | 92.06 | 94.36 | 94.1 |
| $C_8$ (octene) selectivity (wt %)[3] | 80.22 | 80.05 | 82.85 | 83.99 | 81.2 | 81.72 |
| Trimethylpentene fraction (wt %)[4] | 6.45 | 10.67 | 10.97 | 11.16 | 16.36 | 16.61 |

[1]The remainder of the feedstock consists of n-butane and isobutane.
[2]The weight percent is expressed with respect of the total weight of the feedstock ($C_4$ alkenes + n-butane and isobutane).
[3]The weight percent is expressed with respect of total weight of oligomeric product obtained (regardless of carbon number).
[4]The weight percent is expressed with respect of the total weight of octene oligomers obtained.

We claim:

1. A process for oligomerising alkenes having from 3 to 6 carbon atoms which comprises contacting a feedstock comprising
   a) one or several alkenes having x carbon atoms, and
   b) optionally, one or several alkenes having y carbon atoms, x and y being different, with a catalyst containing a zeolite of the MFS structure type, under conditions to obtain selectively an oligomeric product, in which
   i) when the feedstock contains only alkenes having x carbon atoms, said oligomeric product contains at least 60 wt % of oligomers having 2x or 3x carbon atoms, or
   ii) when the feedstock contains alkenes having x carbon atoms and alkenes having y carbon atoms, said oligomeric product contains a mixture of oligomers containing predominant amounts of oligomers having x+y carbon atoms and of oligomers having 2x or 3x carbon atoms,
the percentages by weight being expressed with respect to the total weight of alkenes in the feedstock,
wherein the process is carried out at a temperature of from 125 to 175° C. when the feedstock contains only alkenes with 3 carbon atoms and of from 140 to 240° C. when the feedstock comprises at least one alkene wit 4 or more carbon atoms.

2. A process according to claim 1, characterized in that the total amount of oligomers having x+y carbon atoms and of oligomers having 2x or 3x carbon atoms represents at least 45 wt % of the oligomeric product, based on the total weight of alkenes in the feedstock.

3. A process according to claim 2, characterized in that the feedstock further comprises from 0.05 to 0.25 mol % water, preferably from 0.06 to 0.20 mol % water, most preferably from 0.10 to 0.20 mol % water based on the total hydrocarbon content of the feedstock.

4. A process according to claim 1, characterized in that the zeolite is a ZSM-57 in proton form.

5. A process according to claim 1, characterized in that the pressure is from 5 to 10 MPa.

6. A process according to claim 1, characterized in that the weight hourly space velocity (WHSV) is from 0.1 to 20.

7. A process according to claim 1, characterized in that alkene conversion is from 65 to 95 wt % based on the total weight of alkene in the feedstock.

8. A process according to claim 1, characterized in that the molar ratio of alkenes having x carbon atoms relative to alkenes having y carbon atoms is from 10:90 to 90:10.

9. A process according to claim 1, characterized in that the alkenes are selected from propene, butenes or a mixture of butenes and pentenes.

10. A process according to claim 1, characterized in that the feedstock comprises a mixture of linear and branched alkenes of the same carbon number.

11. A process according to claim 10, characterized in that the feedstock comprises a mixture of linear and branched butenes.

12. A process according to claim 11, characterized in that isobutylene represents from 12 to 34 wt % of the total weight of the feedstock.

13. A process according to claim 12, characterized in that the oligomeric product contains from 8 to 25 wt % trimethylpentenes with respect to the total weight of octenes present in the oligomeric product.

14. An octene composition wherein the octene oligomers with tetra-substituted double bonds represents between 10 and 15 mole % of the total amount of octene oligomers.

15. An octene composition according to claim 14, characterized in that the average branchiness of the octene oligomers is between 1.60 and 1.85.

16. A process according to claim 1, characterized in that the oligomeric product is further submitted to any one or more of the following steps: fractionation, hydrogenation, hydroformylation, oxidation, carbonylation, etherification, epoxidation, hydration.

17. A higher alcohol obtained by hydroformylation and hydrogenation of the oligomeric product obtained by the process according to claim 1.

18. A process for the preparation of an ester of a polycarboxylic acid in which the higher alcohol of claim 17 is reacted with a polycarboxylic acid to make a polycarboxylic ester.

19. An ester of a polycarboxylic acid made by the process according to claim 18.

* * * * *